(12) United States Patent
Shiau

(10) Patent No.: US 6,418,778 B1
(45) Date of Patent: Jul. 16, 2002

(54) GAS DETECTOR EQUIPPED WITH FEEDBACK FUNCTION

(76) Inventor: Jong-Jiing Shiau, 11F, No. 288-2, Ta-Ya Rd., Taichung (TW)

( * ) Notice: Subject to any disclaimer, the term of this patent is extended or adjusted under 35 U.S.C. 154(b) by 0 days.

(21) Appl. No.: 09/793,780

(22) Filed: Feb. 26, 2001

(51) Int. Cl.[7] .......................... G01N 19/10; G01N 27/26
(52) U.S. Cl. ...................................... 73/23.23; 204/425
(58) Field of Search ............................. 73/31.05, 23.21, 73/23.23, 23.36; 340/286.5; 204/425

(56) References Cited

U.S. PATENT DOCUMENTS

| | | | | |
|---|---|---|---|---|
| 5,808,541 A | * | 9/1998 | Golden .................. | 340/286.05 |
| 6,059,947 A | * | 5/2000 | Kato et al. .................. | 204/425 |
| 6,120,663 A | * | 9/2000 | Kato et al. .................. | 204/401 |
| 6,290,829 B1 | * | 9/2001 | Kato et al. .................. | 204/425 |

* cited by examiner

Primary Examiner—Hezron Williams
Assistant Examiner—Jay Politzer
(74) Attorney, Agent, or Firm—Bacon & Thomas

(57) ABSTRACT

A gas detector equipped with a sensor-monitoring feedback function includes a casing and a base board housing a circuit board therein. The circuit board supports a plurality of electronic elements, including a processor unit consisting of a micro control chip (MCU), two output units including a plurality of LED lights and a buzzer, an input unit including a power supply, a voltage stabilizer and a power breaker circuit, an amplification circuit, a sensor and a detection circuit. The detection is capable of monitoring the sensor for normal function and service, and providing feedback constantly so that users will be alerted immediately to malfunction or out of order condition that necessitate repairs and replacement thereby giving users the best possible protection. The gas detector of the invention will also automatically cutoff electricity supply to the sensor for preventing a gas explosion.

4 Claims, 4 Drawing Sheets

GAS DETECTOR EQUIPPED WITH FEEDBACK FUNCTION

BACKGROUND OF THE INVENTION

This invention relates to a gas detector and particularly a safety gas detector that is capable of constantly performing a sensor monitoring feedback function for detecting and alerting persons of abnormal conditions, operation status and gas leakage, and for cutting off sensor electricity to prevent a gas explosion to enhance safety.

In the modern society we are living today, gas ranges, stoves, and water heaters are widely used in many households. While they are very convenient to use, many people tend to take them for granted and overlook the potential risks involved. As a result, accidents of gas intoxication or explosion resulting from gas leakage happen frequently. To prevent an accident or tragedy from occurring, a wide variety of gas detectors have been developed and introduced on the market. However, they mostly have the following drawbacks:

1. Conventional gas detectors mostly use a constantly lit lamp to indicate gas leakage. People's alertness tends to drop when lighting is constant and unchanged, and the lighting may even mistakenly be viewed as a detector malfunction.
2. Conventional gas detectors do not have a feedback system. It could happen that the electronic elements have been damaged after a certain time period but the lighting is still on and without the user's awareness.
3. Conventional gas detector sensors employ expansion of heated platinum to trigger an alarm. However, heated platinum could ignite highly concentrated leaking gas to explode and result in severe damage or other consequences.

SUMMARY OF THE INVENTION

In view of the aforesaid disadvantages, it is therefore an object of this invention to provide a gas detector that is equipped with a feedback function for constantly detecting if the detector itself has been functioning properly, and to produce an alarm immediately once it detects gas leaking, and that is able to automatically cutoff sensor electricity after a preset time frame for preventing a gas explosion from taking place to ensure safety.

Another object of this invention is to use running Light Emitting Diode (LED) lights to indicate self-detecting status, and to produce a blinking light and audio alarm through a buzzer once a gas leak is detected to alert people more effectively.

To attain the aforesaid objects, the gas detector of this invention mainly includes a casing and a base board to house a circuit board therein. The circuit board has a plurality of electronic elements which include a processor unit made up of a micro control chip (MCU), two output units including a plurality of LED lights and a buzzer, an input unit including a power supply, a voltage stabilizer and a power breaker circuit, an amplification circuit for an execution unit, a sensor and a detection circuit. By means of the construction set forth above, this invention may constantly feed back to determine if the detector itself is functioning properly or if the detector's effective service life has expired and needs replacement. As a result, the detector will be constantly kept in a proper working condition to give users the best possible safety protection by providing an immediate gas leakage alert, and by cutting off sensor electricity after a preset time for preventing a gas explosion.

BRIEF DESCRIPTION OF THE DRAWINGS

The invention, as well as its many advantages, may be further understood by the following detailed description and drawings.

DESCRIPTION OF THE PREFERRED EMBODIMENT

Figure 1:
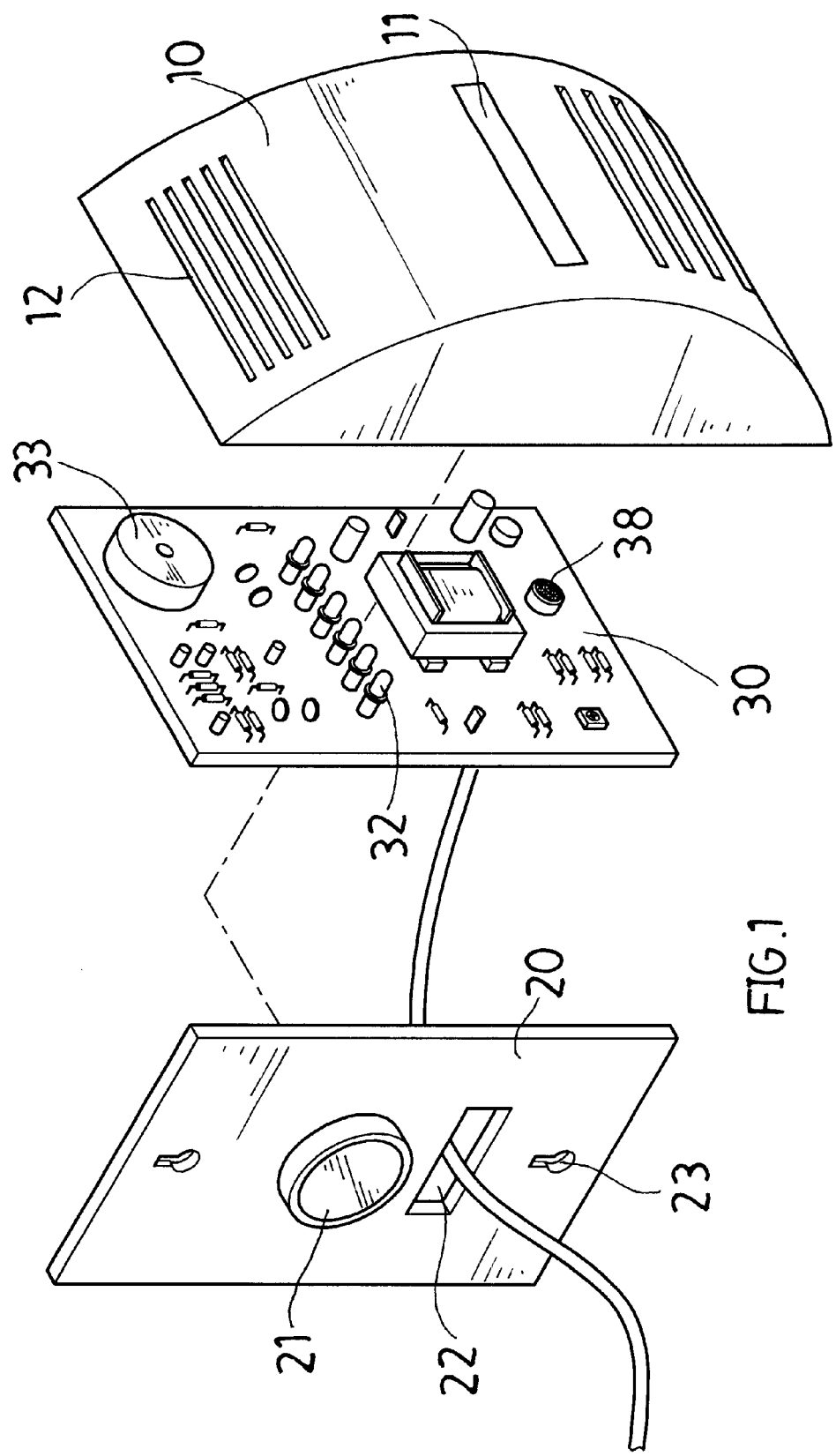
FIG. 1 is an exploded view of this invention.
Figure 2:
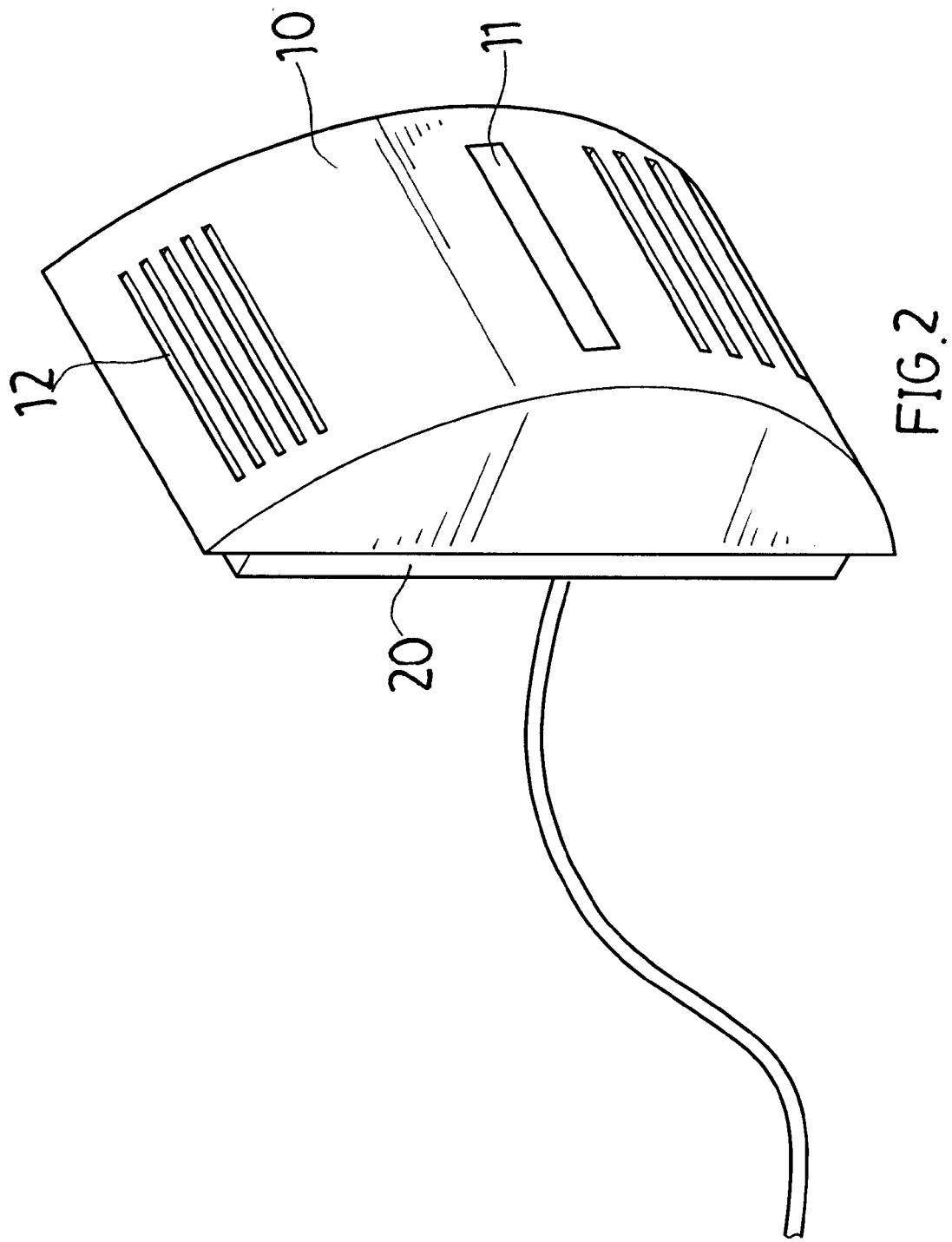
FIG. 2 is a perspective view of this invention.
Figure 3:
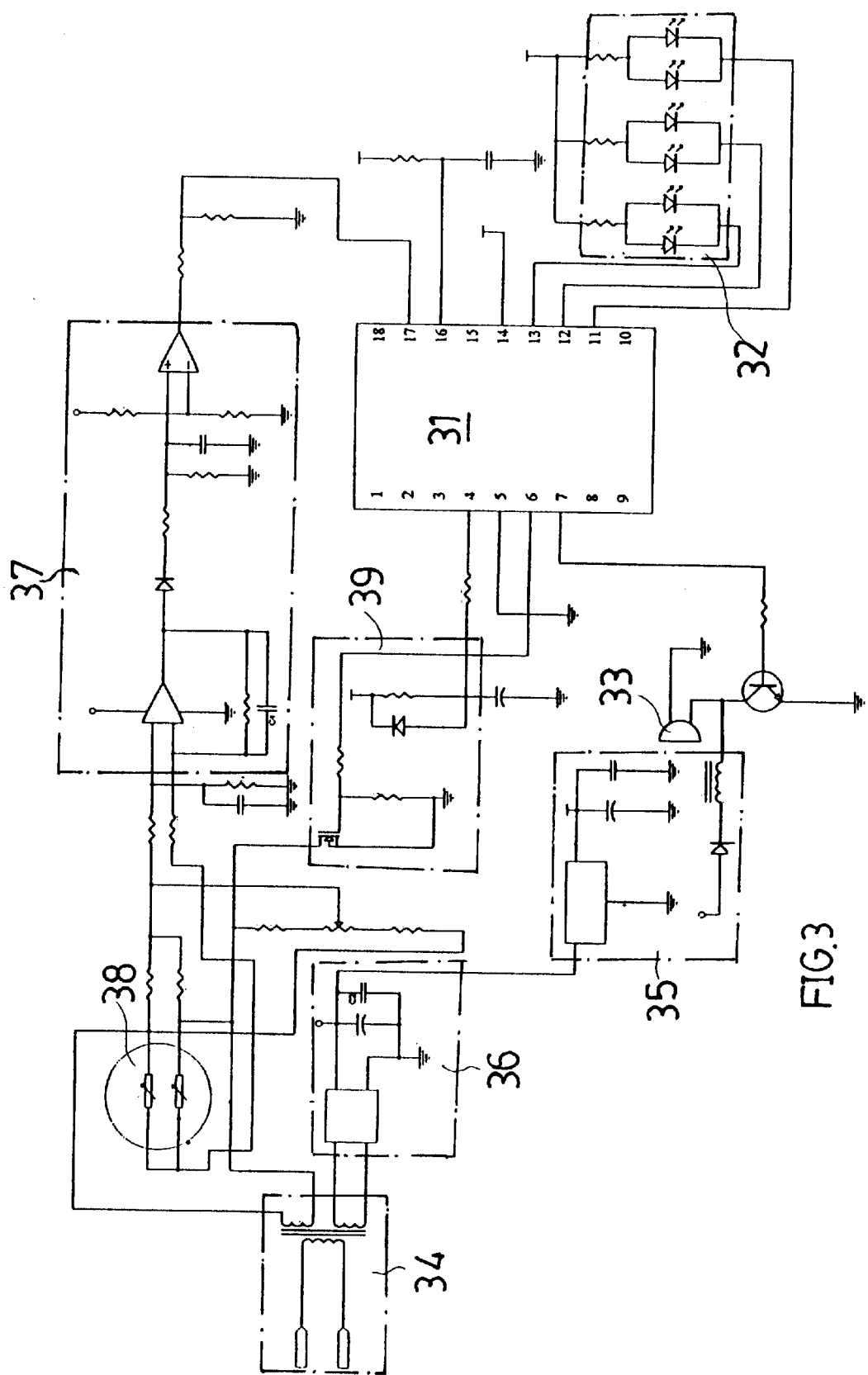
FIG. 3 is a circuit diagram of this invention.
Figure 4:
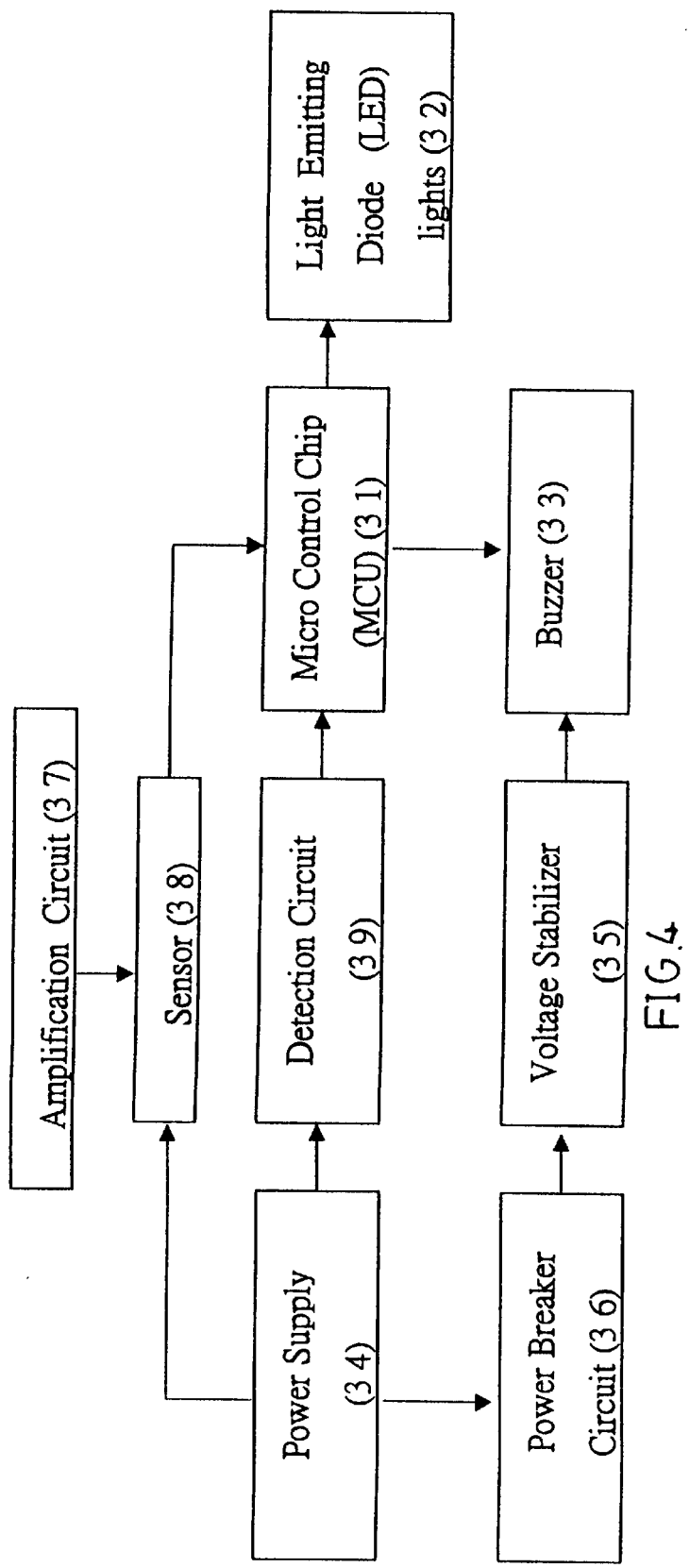
FIG. 4 is a circuit block diagram of this invention.

Referring to FIGS. 1 through 4, the gas detector according to this invention includes mainly a casing 10 and a base board 20 to house a circuit board 30 therein.

The casing 10 is hollow and has a viewing window 11 and slot openings 12 located at two sides of the viewing window 11.

The base board 20 covers one side of the casing 10 and has an outside surface attached to a magnet 21 at the center thereof for the base board 20 (and consequently the detector) to be mounted on the metal casing of a water heater or gas stove or the like. The base board 20 further has an opening 22 adjacent the magnet 21 for the power supply wires of the circuit board 30 to pass through and two mounting bores 23 located at two ends thereof for engaging with screws or nails to mount the base board 20 on a wall or ceiling.

The circuit board 30 constitutes a plurality of electronic elements, including a processor unit which has a micro control chip (MCU) 32 (now commercially available and supplied by ASUS or ACER corporations in Taiwan), two output units including a plurality of LED lights 32 and a buzzer 33, an input unit including a power supply 34, a voltage stabilizer 35 and a power breaker circuit 36, an amplification circuit 37 for an execution unit (not shown), a sensor 38 and a detection circuit 39.

When in use, the power supply 34 supplies electric power as required, the MCU 31 controls the LED lights 32 to display in a running light fashion. Under normal conditions. the MCU 31 activates the detection circuit 39 to sense and check if the whole circuitry is functioning properly. The sensor 38 has a service life of about 9,000 to 12,000 hours when operating continuously. When the detection circuit 39 detects that the sensor circuitry is breaking down or is out of order, the detection circuit 39 will notify the MCU 31 which will activate the buzzer 33 to generate an audio alarm to alert users that the detector is not functioning properly and needs repairs or replacements.

When the sensor 38 detects gas leakage, it responds immediately to the MCU 31 by activating the buzzer 33 to generate a high pitch audio alarm. At the same time, the LED lights 32 will produce a blinking light to serve as a double alarm function.

The sensor 38 operates by heated expansion of platinum under gas fire. As the gas might be ignited by the heated platinum and explode when the gas concentration increases, this invention further includes a power breaker circuit 36 which will cutoff power supply to the sensor 38 when the MCU 31 activates the buzzer 33 for preventing the platinum from continuously heating.

The construction of this invention set forth above has the following advantages:

1. This invention is capable of monitoring itself for normal function and service, and of providing feedback constantly so that any malfunction or out of order will cause users to be alerted immediately for repairs or replacement, thereby giving users the best possible protection.

2. This invention is capable of indicating a gas leakage immediately, and will cutoff electricity supply to the sensor for preventing a gas explosion.
3. This invention uses LED lights to replace conventional illumination light and may last longer and consume less electric power.
4. This invention provides a double effect alarm for abnormal conditions by providing a blinking light and audio alarm, and is more effective.
5. The running light and blinking light indication of the LED lights are more effective for alerting of abnormal situations and are less likely to be read mistakenly.
6. In addition to detecting natural gas, this invention may be used for detecting any other combustible gases.
7. This invention may be activated and function immediately once electric power supply is provided. It is a great improvement over conventional gas detectors which usually need about two minutes of warm up time.
8. This invention may be attached to the metal casing of a water heater or gas stove, or be mounted on the wall or ceiling.

What is claimed is:

1. A gas detector having a sensor monitoring feedback function, comprising:
   a casing mounted on a base board;
   a circuit board housed in the casing; and
   a plurality of electronic elements mounted on the circuit board,
   wherein said plurality of electronic elements includes:
      a processor unit;
      a sensor;
      means including an alarm circuit and output elements for generating an alarm when said sensor senses a gas leak;
      means including a detection circuit connected to the sensor and to the processor unit for monitoring said sensor;
      means for generating an additional alarm when said detection circuit detects that said sensor has malfunctioned.

2. The gas detector of claim 1, wherein the processor unit includes a micro control chip (MCU), the output elements include a plurality of LED lights and a buzzer, and the electronic elements further comprise an input unit that includes a power supply and a voltage stabilizer, and an execution unit that includes an amplification circuit connected between the sensor and the micro control chip.

3. The gas detector of claim 1, wherein the casing is hollow and has a viewing window at a center thereof and slot openings located at two sides of the viewing window.

4. The gas detector of claim 1, wherein the base board has an outside surface, wherein a magnet is attached to a center of the outside surface, and wherein the base board further includes an opening adjacent the magnet and two mounting bores located at two ends of the base board.

* * * * *